US006231560B1

(12) United States Patent
Bui et al.

(10) Patent No.: US 6,231,560 B1
(45) Date of Patent: May 15, 2001

(54) METHOD AND APPARATUS FOR AUTOMATICALLY CONTROLLING THE LEVEL OF MEDICATION

(75) Inventors: Tuan Bui, Green Oaks; Doron Levitas, Chicago; Stephen L. Axel, Deerfield, all of IL (US)

(73) Assignee: Baxter International Inc, Deerfield, IL (US)

( * ) Notice: Subject to any disclaimer, the term of this patent is extended or adjusted under 35 U.S.C. 154(b) by 0 days.

(21) Appl. No.: 09/248,492

(22) Filed: Feb. 10, 1999

(51) Int. Cl.[7] .................................................. A61M 25/00
(52) U.S. Cl. ............................ 604/500; 604/503; 604/66
(58) Field of Search ................................. 604/65, 66, 67, 604/30, 31, 131, 151, 500, 503; 417/2, 53, 63

(56) References Cited

U.S. PATENT DOCUMENTS

| 3,739,943 | 6/1973 | Wilhelmson et al. ................. 222/59 |
| 3,858,574 | 1/1975 | Page ................................. 128/205 T |

(List continued on next page.)

FOREIGN PATENT DOCUMENTS

WO 98/19734   5/1998   (WO) .

OTHER PUBLICATIONS

A.H. McMorris, J.L. Kelleway, B. Tapadia and E. L. Dohmann, "Are Process Control Rooms Obsolete?", taken from Control Engineering, pp. 42–47, Jul., 1971.

Abbott Laboratories, The Blue Line System, Lifecare, copyright, 1990.

L.C. Sheppard, "Computer Based Clinical Systems: Automation and Integration," taken from 39th ACEMB, Sep. 13–16, 1986; pp. 73–75.

"Block Medical: Growing With Home Infusion Therapy," taken from Invivo, The Business and Medicine Report, Apr., 1991; pp. 7–9.

"IEEE–488 and VXIbus Control, Data Acquisition, and Analysis . . . the Most Choices," select pages taken from National Instruments, Application Software Products and Application Software Overview, (1991) 17 pages.

"LabView®2 User Manual; Chapter 2, The Front Panel," taken from National Instruments Corporation, Jan., 1990; pp. 1–36.

J. C. Crone, Jaromir Belic and Roger W. Jelliffe, M.D., "A Programmable Infusion Pump Controller," taken from 30th Annual Conference on Engineering in Medicine and Biology, Nov. 5–9, 1977; pp. A–35827 through A–35837.

Selective portions of Chapter 9 of Mayhew, "Principles and Guidelines In Software User Interface Design," Prentice Hall PTR, Englewood Cliffs, New Jerssey, 1992.

Electronic's Article of Feb., 1990, by Jack Shandle, entitled "Who Will Dominate the Desktop in the '90s," pp. 48–50.

Chapter 5 entitled "Direct Manipulation" from Shneiderman "Designing the User Interface: Strategies for Effective Human–Computer Interaction," Addison–Wesley Publishing Company, Second Edition, ©1992, reprinted with corrections 1993.

Literature of Baxter's MultiPlex™ Series 100 Fluid Management System, 2 pp., no date listed.

Literature of Baxter "Introducing MultiPlex™ Series 100 Fluid Management System," copyright 1988.

Literature describing Baxter's Flo–Gard® 6201 Volumetric Infusion Pump, copyright 1992.

(List continued on next page.)

Primary Examiner—John D. Yasko
(74) Attorney, Agent, or Firm—Wallenstein & Wagner, Ltd.

(57) ABSTRACT

A method and apparatus which captures relevant information pertaining to a patient's physiological conditions, automatically adjusts the amount of medication to optimize the treatment of pain and improve the patient's quality of life is described.

18 Claims, 7 Drawing Sheets

U.S. PATENT DOCUMENTS

| | | |
|---|---|---|
| 3,910,257 | 10/1975 | Fletcher et al. ............... 128/2.1 A |
| 4,173,971 | 11/1979 | Karz ............................ 128/702 |
| 4,392,849 | 7/1983 | Petre et al. . |
| 4,413,314 | 11/1983 | Slater et al. .................. 364/188 |
| 4,449,538 | 5/1984 | Corbitt et al. ................. 128/760 |
| 4,531,527 | 7/1985 | Reinhold, Jr. et al. ........ 128/696 |
| 4,551,133 | 11/1985 | Zegeers de Beyl et al. . |
| 4,561,443 | 12/1985 | Hogrefe et al. ............ 128/419 PG |
| 4,586,260 | 5/1986 | Baxter et al. ................. 33/125 C |
| 4,624,661 | 11/1986 | Arimond ...................... 604/151 |
| 4,676,776 | 6/1987 | Howson ........................ 604/31 |
| 4,696,671 | 9/1987 | Epstein et al. ................ 604/67 |
| 4,731,051 | 3/1988 | Fischell ........................ 606/67 |
| 4,756,706 | 7/1988 | Kerns et al. .................. 604/66 |
| 4,797,840 | 1/1989 | Fraden .......................... 364/557 |
| 4,803,625 | 2/1989 | Fu et al. .................... 364/413.03 |
| 4,810,243 | 3/1989 | Howson ........................ 604/31 |
| 4,828,545 | 5/1989 | Epstein et al. ................ 604/66 |
| 4,850,972 | 7/1989 | Schulman et al. ............ 604/151 |
| 4,865,584 | 9/1989 | Epstein et al. ................ 604/67 |
| 4,901,221 | 2/1990 | Kodosky et al. ............. 364/200 |
| 4,925,444 | 5/1990 | Orkin et al. .................. 604/80 |
| 4,933,843 | 6/1990 | Scheller et al. ............ 364/413.01 |
| 4,942,514 | 7/1990 | Miyagaki et al. ............ 364/190 |
| 4,952,928 | 8/1990 | Carroll et al. .............. 340/825.54 |
| 4,995,268 | 2/1991 | Ash et al. ................... 73/861.05 |
| 5,002,055 | 3/1991 | Merki et al. . |
| 5,038,800 | 8/1991 | Oba .............................. 128/904 |
| 5,069,668 | 12/1991 | Boydman . |
| 5,078,683 | 1/1992 | Sancoff et al. ............... 604/67 |
| 5,100,380 | 3/1992 | Epstein et al. ................ 604/67 |
| 5,109,849 | 5/1992 | Goodman et al. ............ 128/633 |
| 5,115,133 | 5/1992 | Knudson ...................... 250/341 |
| 5,116,312 | 5/1992 | Blankenship et al. ........ 604/66 |
| 5,137,023 | 8/1992 | Mendelson et al. .......... 128/633 |
| 5,152,296 | 10/1992 | Simons ......................... 128/670 |
| 5,153,827 | 10/1992 | Coutré et al. .............. 364/413.02 |
| 5,155,693 | 10/1992 | Altmayer et al. ............. 364/550 |
| 5,165,874 | 11/1992 | Sancoff et al. ............... 417/474 |
| 5,167,235 | 12/1992 | Seacord et al. ............... 128/664 |
| 5,191,891 | 3/1993 | Righter ......................... 128/710 |
| 5,207,642 | 5/1993 | Orkin et al. .................. 604/65 |
| 5,213,099 | 5/1993 | Tripp, Jr. ...................... 128/633 |
| 5,226,425 | 7/1993 | Righter ......................... 128/710 |
| 5,230,623 | 7/1993 | Guthrie et al. ................ 433/72 |
| 5,256,157 | 10/1993 | Samiotes et al. ............. 604/246 |
| 5,291,190 | 3/1994 | Scarola et al. .............. 340/825.06 |
| 5,295,062 | 3/1994 | Fukushima ................... 364/188 |
| 5,297,554 | 3/1994 | Glynn et al. .................. 128/665 |
| 5,317,506 | 5/1994 | Coutré et al. ................. 364/413 |
| 5,338,157 | 8/1994 | Blomquist .................... 417/2 |
| 5,361,758 | 11/1994 | Hall et al. ..................... 128/633 |
| 5,368,562 | 11/1994 | Blomquist et al. ........... 604/65 |
| 5,376,070 | 12/1994 | Purvis et al. .................. 604/31 |
| 5,378,231 | 1/1995 | Johnson et al. ............... 604/67 |
| 5,395,321 | 3/1995 | Kawahara et al. ............ 604/67 |
| 5,395,329 | 3/1995 | Fleitschhackor et al. ..... 604/95 |
| 5,400,246 | 3/1995 | Wilson et al. ................. 364/146 |
| 5,412,400 | 5/1995 | Takahara et al. .............. 345/119 |
| 5,423,748 | 6/1995 | Uhala . |
| 5,429,602 | 7/1995 | Hauser .......................... 604/65 |
| 5,469,855 | 11/1995 | Pompei et al. ................ 128/664 |
| 5,482,446 | 1/1996 | Williamson et al. ......... 417/474 |
| 5,485,408 | 1/1996 | Blomquist .................... 364/578 |
| 5,509,422 | 4/1996 | Fukami ......................... 128/670 |
| 5,522,396 | 6/1996 | Langer et al. ................. 128/696 |
| 5,544,651 | 8/1996 | Wilk ............................. 128/633 |
| 5,558,638 | 9/1996 | Evers et al. ................... 604/66 |
| 5,573,506 | 11/1996 | Vasko ........................... 604/65 |
| 5,582,593 | 12/1996 | Hultman ....................... 604/65 |
| 5,643,212 | 7/1997 | Coutré et al. . |
| 5,681,285 | * 10/1997 | Ford et al. .................... 604/151 |
| 5,840,026 | * 11/1998 | Uber, III et al. .............. 604/66 X |
| 5,935,099 | * 8/1999 | Peterson et al. .............. 604/65 |
| 6,010,483 | 1/2000 | Spencer . |

OTHER PUBLICATIONS

Literature of I–Flow Corporation advertising its Vivus 4000 Infusion System.

One–page article by Jerry Hirsch entitled "Portable IV Frees Patients," printed in The Orange County Register, D section, Nov. 21, 1991.

Bedder, et al., "Cost Analysis of Two Implantable Narcotic Delivery Systems," Journal of Pain and Symptom Management, vol. 6, No. 6, Aug., 1991, pp. 368–373.

Peter Lord, Hossein Allami, Mark Davis, Raul Dias, Patrice Heck, and Robert Fischell, pp. 66–71 from book chapter entitled "MiniMed Technologies Programmable Implantable Infusion System," describing clinical trials from Nov., 1986.

"IMED®Status™ Infusion Management System," 6 page brochure, IMED Corporation, San Diego, CA, no date listed.

James D. Foley and Andries Van Dam "Fundamentals of Interactive Computer Graphics," selected pages from Chapters 1 and 2, Addison–Wesley Publishing Company, ©1982, reprinted with corrections 1983.

* cited by examiner

METHOD AND APPARATUS FOR AUTOMATICALLY CONTROLLING THE LEVEL OF MEDICATION

BACKGROUND OF THE INVENTION

The present invention is directed to a method and apparatus for automatically adjusting the medication level for a patient, and more particularly to adjusting the basal rate and the bolus rate of administration in a patient control analgesia mode based on the patient's pain intensity.

Infusion pumps are used to automatically administer liquid medicants to patients. The liquid medicant is supplied from a source of medicant and delivered to the patient via a catheter or other injection device. The manner in which the liquid medicant is infused is controlled by the infusion pump, which may have various modes of infusion. An infusion pump typically can operate in five basic modes of infusion: 1) a continuous mode in which the pump delivers a single volume at a single rate; 2) an auto-ramp mode in which the pump delivers liquid medicant at a rate that gradually increases to a threshold rate, remains at the threshold rate for a period of time, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain controlled analgesic (PCA) mode during which the pump will periodically infuse boluses of an analgesic in response to requests by the patient.

In pain control analgesia, a pain relief medication or analgesic is delivered to the patient via an infusion pump into a patient's intravenous line, or to the epidural space or an interthecal space. Usually the medication is delivered at a constant rate, called the basal rate. The physician programs the basal rate into the pump. However, the patient is allowed, within bounds, to give himself additional medication, to reduce the pain level, if desired. This is done via a bolus cord. The patient presses a button on the bolus cord and the pump delivers a small bolus of medication to the patient. The maximum level of medication given in response to each press of the bolus cord button, is programmed into the pump by the physician. The maximum number of button presses which will result in a discharge of a bolus is also programmed into the pump by the physician. Once the pump is programmed by the physician, the patient can give himself a bolus whenever he needs it, regardless of time between requests. However, if the patient exceeds the maximum number of boluses programmed, any additional requested boluses will not be successful and will not result in the delivery of medication.

The physician limits the amount of medication given to the patient at any one time, and over a period of time, to reduce the level of side effects. Some pain relief medications have highly undesirable side effects, such as nausea, vomiting, itching and confusion, cardiac and respiratory depression or in sufficient quantity, may result in death. Patient functionality, e.g., mobility and awareness, is affected by pain and side effects.

Controlling of the amount of pain medication, i.e., the basal rate, the bolus dose and the maximum number of bolus doses available to the patient is a delicate balance of competing requirements. To increase pain relief, a physician will prescribe greater medication. However, large doses of some pain medication can increase the side effects and can impair patient functionalities. Using a pain medication may reduce pain sufficiently to enable the patient to move about. Using a level of pain medication which produces confusion detracts from the patient's mobility.

During acute care, when the patient is in greater need of additional pain medication, it is important to be able to adjust the PCA basal rate, the bolus rate and the bolus amount more frequently, always taking into account the effect of side effects and impairment of patient functionalities.

Infusion modes are programmed into the infusion pump by the caregiver or physician. In a hospital or other caregiver facility, a physician or caregiver can visit a patient once or twice a day to check if the programmed infusion mode, dose and frequency are providing appropriate relief to the patient. If the patient is receiving medication at home or away from a caregiver facility, such visits may be less frequent. In most of the pre-programmed modes, rechecking the mode, dose and frequency once or twice a day may be sufficient. If the patient is in the PCA mode, however, the patient's condition may vary more, requiring more frequent adjustment and more frequent visits by the physician or caregiver. If the patient is not able to receive additional adjustments or visits from the physician or caregiver, whether in the home or the hospital, the patient may be in extreme pain and may not receive appropriate pain relief for many hours.

U.S. Pat. No. 5,643,212 to Coutre et al. discloses an infusion pump management system in which the patient's physiological signs are used in a biofeedback loop. The system evaluates the patient's physiological signs and suggests alternate infusion treatment based on those signs. The proposed modifications are then sent to the operator for confirmation. Delivery rate changes are made by the operator (physician or caregiver), so the patient must wait until the operator can evaluate the proposed changes before the patient can receive any relief.

There is a need for an automatic method of adjusting the medication level in patient control analgesia taking into account the patient's pain level, side effects and any impairment of functionalities. There is a need for an apparatus for automatically adjusting the medication level in response to input from a patient regarding his pain level, side effects and impairment of functionalities, without having to contact the caregiver or physician. There is a need for a method of automatically adjusting the medication level in patient control analgesia using a predetermined set of criteria which is patient specific, yet provides the patient the ability to have his medication adjusted without having to contact a caregiver or physician.

SUMMARY OF THE INVENTION

A preferred embodiment of the invention is directed to a method and apparatus which captures relevant information pertaining to pain level, side effects and patient impairment and automatically adjusts the amount of medication, within a pre-determined level selected by the patient's physician, to optimize the treatment of pain and improve the patient's quality of life.

Prior to prescribing pain medication to be provided via a programmable infusion pump, the physician or caregiver must program the pump for the specific patient. In addition to programming in the specifics of a PCA treatment, by programming in basal rate, maximum number of bolus doses and volume amount of each bolus dose, in accordance with the preferred embodiment of the invention, the programmable infusion pump includes a routine for modifying the PCA treatment. The PCA modification routine stores pre-programmed values of basal rate, bolus number and amounts for the specific patient, which are input the by physician or caregiver. The routine also includes a pain relief algorithm which modifies the PCA treatment in response to input regarding the patient's pain level, side effects and function impairment.

Pain level can be determined using either of two methods, or by a combination of the two methods. In a first method, the programmable infusion pump stores the number of bolus requests by the patient and whether or not they resulted in delivery of a bolus over a prescribed period of time. If the patient makes a significant number of bolus requests over the maximum permitted in a short period of time, this is used as an indication that the patient's pain level is high. A second method of determining pain level is to query the patient directly and evaluate the patient's responses. A combination of both methods can also be used.

Side effect information can be determined in either of two ways, or by using a combination of the two. In the first method, the patient is asked various questions about specific side effects. In a second method, if the patient is in a hospital or other facility with a caregiver, the caregiver records the patient's responses to inquiries about side effects on the patient's chart. The caregiver may also record his observations about the patient's side effects onto the patient's chart. Data recorded on the patient's chart can later be input to the programmable infusion pump. A combination of both methods can also be used.

Similarly, information regarding impairment of patient functionality can be input by the patient in response to specific queries prompted by the infusion pump, or by a caregiver or by a combination of both.

After completion of inputting all data, the data is processed by the algorithm, and the patient's PCA medication rate is conformed to the algorithm or adjusted if indicated by the algorithm.

In an alternative embodiment of the invention, if the patient's vital signs are being monitored, they can be used to provide data regarding the side effects and patient functionalities. Vital sign data can be input to the programmable infusion pump via a data port, processed by the algorithm and the patient's PCA medication adjusted.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
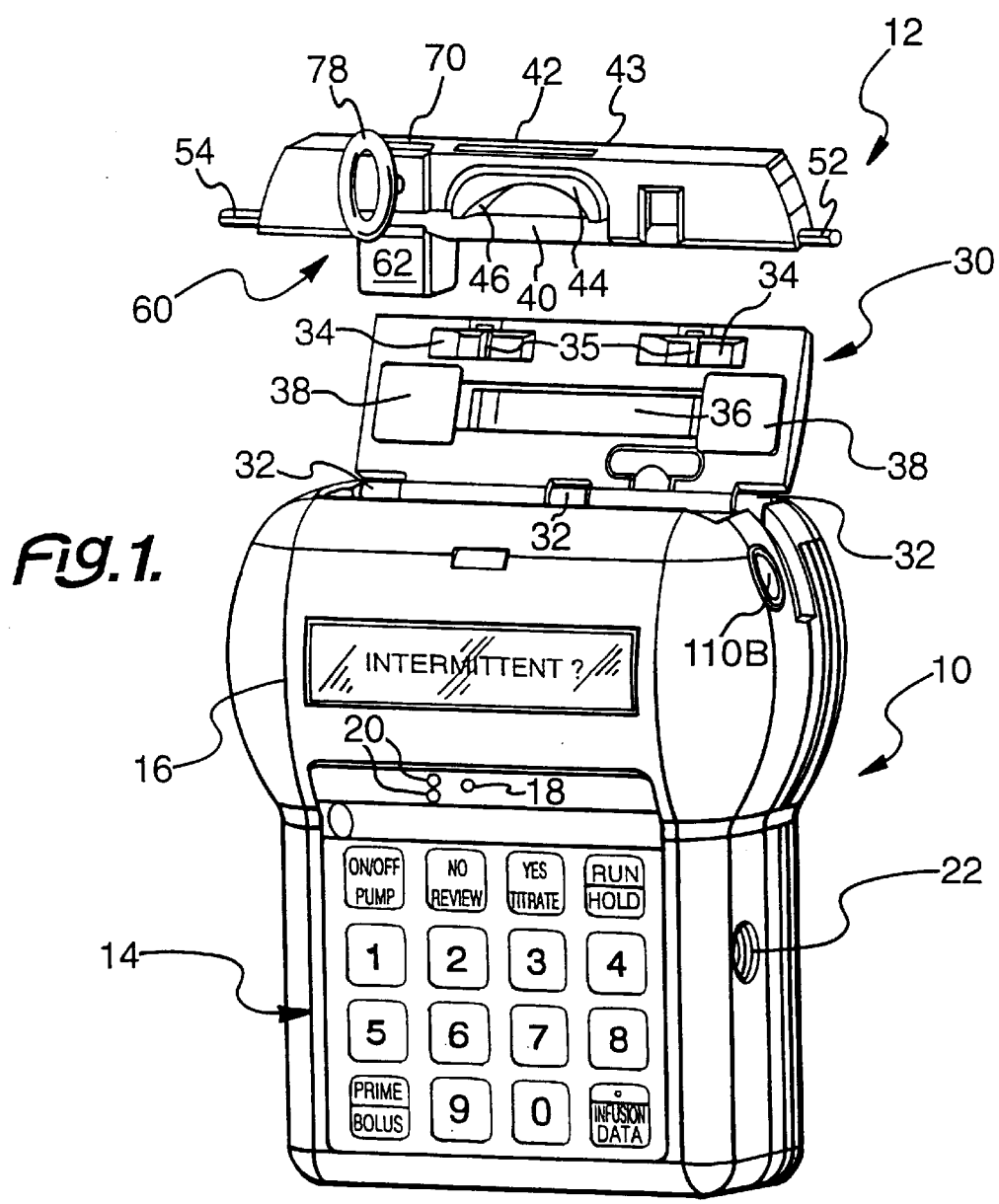
FIG. 1 is a perspective view of an infusion pump embodying the present invention and a cassette which is insertable into the pump.
Figure 1A:
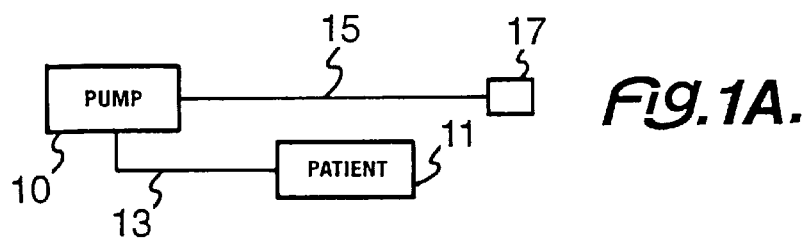
FIG. 1A is a block diagram showing the connection of the infusion pump of FIG. 1 to a patient.

Referring now to the drawings and specifically to FIGS. 1 and 1A, a portable infusion pump embodying the present invention is shown therein and generally identified by reference numeral 10. The infusion pump 10 provides liquid medicant to patient 11 via catheter 13. Bolus cord 15 is connected to pump 10. Patient 11 makes a bolus request by pressing bolus button 17. A signal from bolus button 17 travels down bolus cord 15 to bolus infusion request switch 332 (see FIG. 2) where the request is processed by controller 200 (see FIG. 2).

The infusion pump 10 provides automatic adjustment of a patient's pain medication. A cassette 12 is insertable into the pump 10. The portable pump 10 may be carried in a pouch or other device (not shown) attached to a patient so that the pump 10 may be carried wherever the patient goes.

The infusion pump 10 has a keypad 14 via which a user may input data and commands, a selectively backlighted, dot matrix or LCD display 16 for displaying textual messages to the user, a light sensor 18 for detecting the level of ambient light, and a pair of light-emitting diodes (LED) 20, a green LED for indicating the normal operation of the pump 10 and a red LED for indicating an alarm or abnormal operating condition of the pump 10. As described below, the level of the light sensed by the ambient light sensor 18 is used to control when the display 16 is backlighted. A data port 22, which is preferably an RS-232 port, is used to download and upload data between the pump 10 and a remote controller or other device. Data port 22 would be used to upload vital sign data from a vital sign monitor, such as heart rate, respiration rate, for example.

A door 30 is pivotally attached to the upper portion of the infusion pump 10 via a plurality of hinges 32. An underside 33 of the door 30, which is shown in FIG. 1, has a pair of slots 34 formed therein in which a pair of metal rods 35 are fixed. Each of the metal rods 35 selectively engages a pair of slidable latching members (not shown) to retain the door 30 in the closed position during operation of the pump 10.

An arcuate metal leaf spring 36 is disposed on the underside of the door 30. The two ends 37 of the leaf spring 36 are anchored by a pair of retaining elements 38 fixed to the door 30. When the cassette 12, in which a flexible silicone tube 40 is disposed, is inserted into the pump 10 and the door 30 is closed, the leaf spring 36 makes contact with and applies a downward force on an upper surface 42 of a vertically movable platen 44. As shown in FIG. 1, the upper surface 42 of the platen 44 is disposed within an elongated slot or aperture 43 disposed in the upper surface of the cassette housing 12. The platen 44 has a lower curved surface 46 against which the flexible tube 40 is pressed by a number of rollers disposed on a conventional rotary pump wheel (not shown) to effect peristaltic pumping of liquid through the tube 40.

The cassette 12 has a flow-stop mechanism 60 that automatically clamps the flexible tube 40 shut when the cassette 12 is not disposed in the pump 10 with the silicone tube 40 in its fully engaged position or when the pump door 30 is open. This prevents an open or uncontrolled liquid path being made available between the medicant source and the patient. The flow-stop mechanism 60 has a housing 62.

Infusion Pump Electronics

Figure 2:
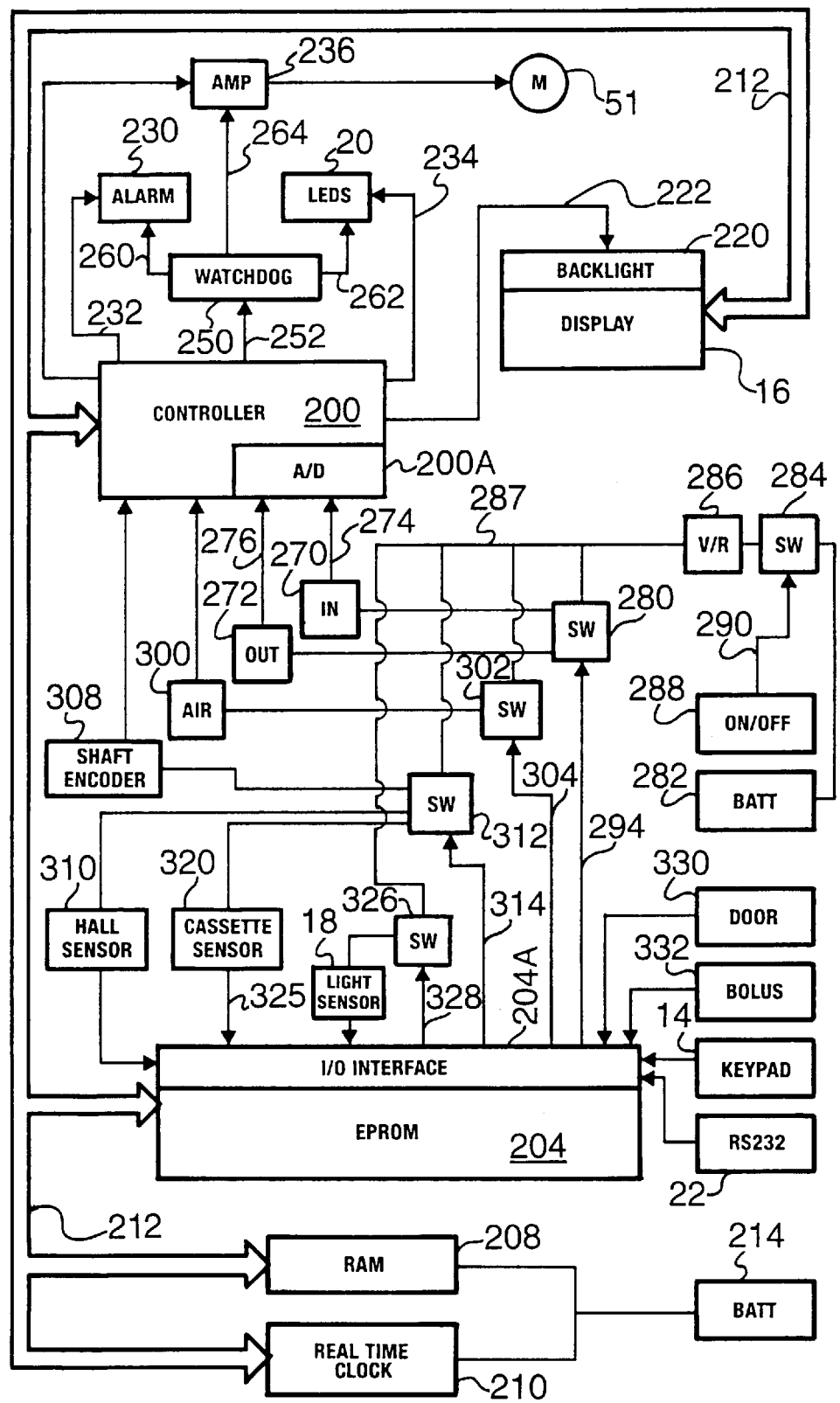
FIG. 2 is a block diagram of the electronic and electrical components of the infusion pump shown in FIG. 1.

Referring to FIG. 2, the infusion pump 10 includes a controller 200 with a built-in analog-to-digital (A/D) converter 200A, an electrically programmable read-only memory (EPROM) 204 having a built-in input/output (I/O) interface 204A, a random-access memory (RAM) 208, a real-time clock 210 and the display 16, all of which are interconnected by a communications bus 212. The display 16 has a backlight 220 which is selectively activated by an enable signal generated on a line 222 interconnecting the controller 200 and the backlight 220. Both the RAM 208 and the real-time clock 210 are connected to a battery 214 which supplies power to them only in the absence of system power (generated by a second battery 282). Since it is always powered, the RAM 208 is a non-volatile memory.

The controller 200, which may be a conventional microcontroller such as an 80C196KB commercially available from Intel Corporation, controls an audible alarm generator 230 via a line 232, the LED's 20 via a line 234, and a pump motor signal amplifier circuit 236 via a line 238. The pump motor signal amplifier circuit 236 is connected to drive the pump motor 51 which drives the rotary pump wheel. During normal operation, the controller 200 also sends a periodic signal to a conventional watchdog timer 250 via a line 252. If the controller 200 should fail to transmit the periodic signal to the watchdog timer 250, which would indicate failure or malfunction of the controller 200, the watchdog timer 250 transmits a signal via a line 260 to cause the alarm 230 to sound, transmits a signal via a line 262 to cause the red LED to be illuminated, and transmits a signal via a line 264 to the amplifier circuit 236 to cause the pump motor 51 to stop.

The pump 10 has a number of sensors which sense various conditions relating to the operation of the pump. These sensors include an input pressure sensor 270 for detecting the liquid pressure within the flexible tube 40 at a point upstream of the rotary pump wheel and an output pressure sensor 272 for detecting the liquid pressure within the flexible tube 40 at a point downstream of the rotary pump wheel. The input pressure sensor 270 generates an analog signal, indicative of the input pressure, which is transmitted to the A/D converter 200A via a line 274. The output pressure sensor 272 generates an analog signal, indicative of the output pressure, which is transmitted to the A/D converter 200A via a line 276. Each of the pressure sensors 270, 272, which detect occlusions with the flexible tube 40 or the tubing 52, 54 connected thereto, may be provided in the form of a strain gauge or beam (not show) which is in contact with the exterior of the flexible tube 40 and a high-gain amplifier (not shown) connected to the strain beam.

The pressure sensors 270, 272 are connected to, and receive power from, a power switch 280 which is connected to a battery 282 through a system power switch 284, a voltage regulator 286, and a system power line 287. The system power switch 284 selectively supplies power from the battery 282 to the voltage regulator 286 based on the state of a pump on/off switch 288 connected to the system power switch 284. The power switch 280 is controlled by the controller 200 via the bus 212, the I/O interface 204A, and a line 294 which interconnects the I/O interface 204A and the power switch 280.

The pump 10 has an air-in-line sensor 300, which may be provided in the form of a conventional piezoelectric transmitter and receiver (not shown) coupled to a sensing circuit (not shown), to detect the presence of any significant air bubbles within the flexible tube 40. The air-in-line sensor 300 receives power from a power switch 302 which is connected to the system power line 287 and controlled by the controller 200 via a line 304 connected to the I/O interface 204a.

The pump 10 has a shaft encoder sensor 308 and a Hall-effect sensor 310 which receive power from a power switch 312 coupled to the system power line 287 and controlled by the controller 200 via a line 314. The shaft encoder sensor 308, which is disposed on the shaft of the motor 51, may be a two-phase motion sensing encoder which provides two signal outputs to the controller 200. The rotational speed of the motor 51 and its direction of rotation are determined by the controller 200 based upon the rate and phase relationship between the two signal outputs. The Hall-effect sensor 310 is disposed adjacent the rotary pump wheel and detects magnetic encoding on the pump wheel for detecting rotation of the wheel. A cassette sensor 320, which is also connected to the power switch 312, detects the type of cassette which is inserted into the pump 10.

Referring to FIG. 2, the ambient light sensor 18 is connected to a power switch 326 which is controlled by the controller 200 via a line 328 from the I/O interface 204A. Signals generated by a door-open sensor 330, a bolus infusion request switch 332, the keypad 14 and the data port 22 are transmitted to the controller 200 via the I/O interface 204A. Although not shown in FIG. 2 for purposes of simplicity, the controller 200, the EPROM 204, the RAM 208, and the display 16 are also connected to and receive power from the system power line 287.

Overall Pump Program Operation

Figure 3:
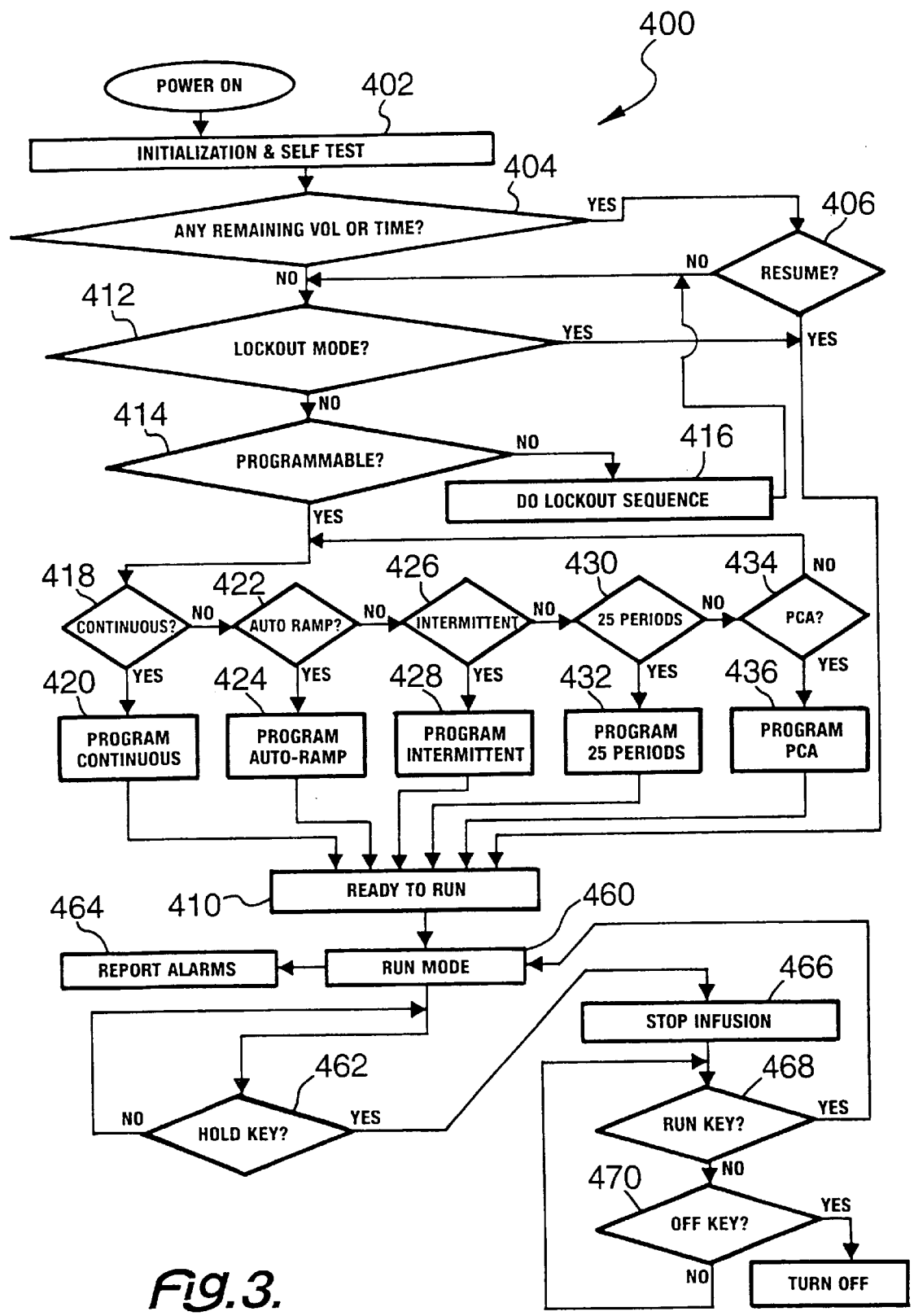
FIG. 3 is a flowchart of the overall operation of the infusion pump shown in FIG. 1.

The operation of the infusion pump 10 is controlled by a computer program stored in the EPROM 204 and executed by the controller 200. The programming of the pump is usually performed by a caregiver following a prescription described by the patient's physician. In some cases, the patient is allowed to alter certain parameters of the pump. A flowchart of the overall operation is illustrated in FIG. 3. Referring to FIG. 3, when the pump 10 is turned on via the on/off switch 288, at step 402 the pump is initialized and a test of the pump operation is performed. The pump 10 may be turned off temporarily during an infusion, in which case the pump 10 may continue the infusion when it is turned back on, as described below. At step 404, if there is any remaining volume of liquid to be infused by the pump or any additional time remaining for an infusion, which would be the case where the pump was temporarily turned off during an infusion, the program branches to step 406, where the caregiver is asked, via a message displayed on the display 16, whether the previous infusion should be resumed. If the caregiver answers yes (via the keyboard 14), the program branches to a ready-to-run step 410. If the previous infusion is not to be resumed, the program branches to step 412.

The infusion pump 10 has a lockout mode in which the patient may be prevented from programming the infusion parameters, such as the volume to be infused or the rate of infusion. For example, the pump 10 could be programmed by a caregiver to deliver a particular infusion having a particular flow profile, flow rate, and volume to be infused. After programming that infusion, the caregiver could place the pump in lockout mode, which would prevent the patient from changing any of the infusion parameters. At step 412, if the pump 10 has been previously placed in lockout mode, the program branches directly to the ready-to-run step 410, bypassing all programming steps.

At step 412, if the pump is not in lockout mode, the program branches to step 414, at which point the program prompts the caregiver, via the display 16, to input whether the patient should be allowed to program the pump during the subsequent infusion. If the pump is not to be programmable, the program branches to step 416 where a lockout sequence is performed by requesting the caregiver to input which infusion modes should be locked out. If the pump is to be programmable by the patient, the program bypasses step 416.

The infusion pump 10 has five basic modes of infusion: 1) a continuous mode in which the pump delivers a single volume at a single rate; 2) an auto-ramp mode in which the pump delivers liquid at a rate that gradually increases to a threshold rate, stays constant at the threshold rate, and then gradually decreases; 3) an intermittent mode in which the pump delivers discrete liquid volumes spaced over relatively long periods of time, such as a liquid volume every three hours; 4) a custom mode in which the pump can be programmed to deliver a unique infusion rate during each of 25 different time periods; and 5) a pain-controlled analgesic (PCA) mode during which the pump will periodically infuse boluses of analgesic in response to periodic requests by the patient, which requests are made via the bolus-request key 332.

At step 418, the pump 10 generates on the display 16 the prompt "Continuous?" to the caregiver. If the caregiver desires to use the pump in its continuous mode, the caregiver answers "yes" via the keypad 14, and the program branches to step 420 at which the continuous mode is programmed by the caregiver by entering a number of infusion parameters, such as the desired infusion rate, the volume to be infused, etc. At step 418, if the caregiver does not want to use the continuous mode, the caregiver answers "No", and the program branches to step 422. Steps 422–436 are generally the same as steps 418 and 420, except that the caregiver may be prompted for different infusion parameters, depending on which of the five possible infusion modes is selected.

Program PCA Mode

Figure 7:
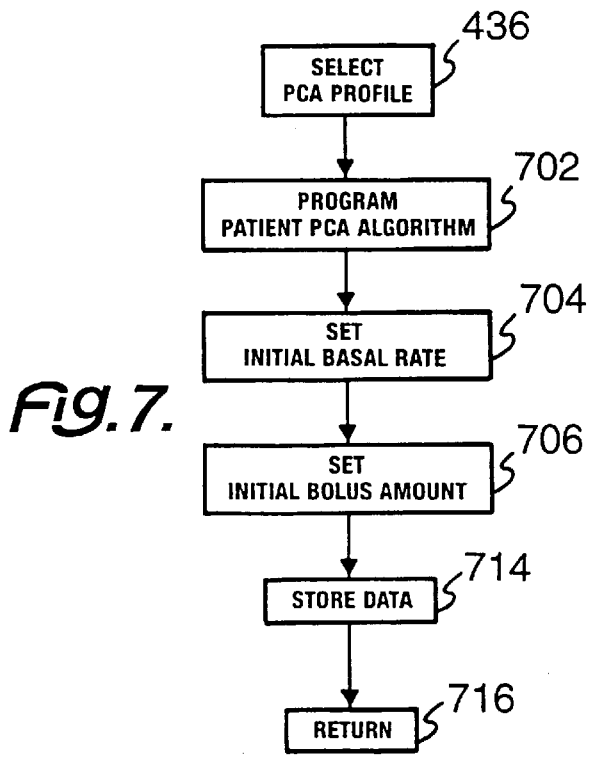
FIG. 7 is a flowchart of the operation of the program PCA mode of the infusion pump shown in FIG. 1.

A flowchart of the operation of the Program PCA mode 436 is shown in FIG. 7. In Pain Control Analgesic (PCA) mode, the caregiver programs the patient's algorithm as provided by the physician (described below), a basal rate which is a continuous basic rate of drug delivery and a bolus amount which is the additional drug that can be delivered on top of, or in addition to, the basal rate at specific time intervals. In step 702, the program prompts the caregiver to program patient algorithm. In step 704, the program prompts the caregiver to program the basal rate. The caregiver inputs an amount to be infused to the patient continuously. After entering the desired rate, e.g. 10 mg/hr, the caregiver then enters the total volume and selects "Limit Med. by # of Dose/hour". The program then prompts the caregiver for the basal amount in step 706. the caregiver enters the desired value. Then the program prompts the caregiver for the maximum number of boluses at step 710. After the caregiver inputs the desired number, the program stores the programmed values at step 714 and returns to the main program at step 716.

Referring back to FIG. 3, after the completion of one of the steps 420, 424, 428, 432 or 436, the program branches to the ready-to-run step 410. During the run mode 460, the pump 10 infuses the patient with a liquid medicant in accordance with the infusion mode selected at one of steps 418, 422, 426, 430, 434 and the infusion parameters entered at one of steps 420, 424, 428, 432, 436. The pump 10 remains in the run mode 460 until the hold key is pressed, as determined at step 462. Upon the occurrence of an alarm condition, an alarm is reported at step 464.

At step 462, if the hold key is pressed, the infusion is stopped at step 466, and the pump 10 waits for the run key to be pressed at step 468 or the on/off switch to be turned off at step 470.

Summarizing the operation described above, if the pump is to be utilized in lockout mode, a caregiver turns the pump on, programs the desired infusion mode at one of steps 420, 424, 428, 432, 436, and then turns the pump off. The programmed infusion parameters will be retained in the nonvolatile memory 208. The caregiver would then turn the pump back on, press the "No" key in response to the "Programmable?" prompt at step 414, enter the lockout information at step 416, and then turn the pump off again. When the patient subsequently turned on the pump to perform the infusion (after a cassette 12 is primed with the liquid to be infused and inserted into the pump), the program would proceed from step 412 directly to the ready-to-run step 410, which would prevent the patient from altering the infusion parameters.

If the lockout mode was not utilized, the caregiver or the patient could turn the pump on, program the desired infusion mode, and then press the "Run" key to start the infusion without every turning the pump off.

Pump Operating System

Figure 4:
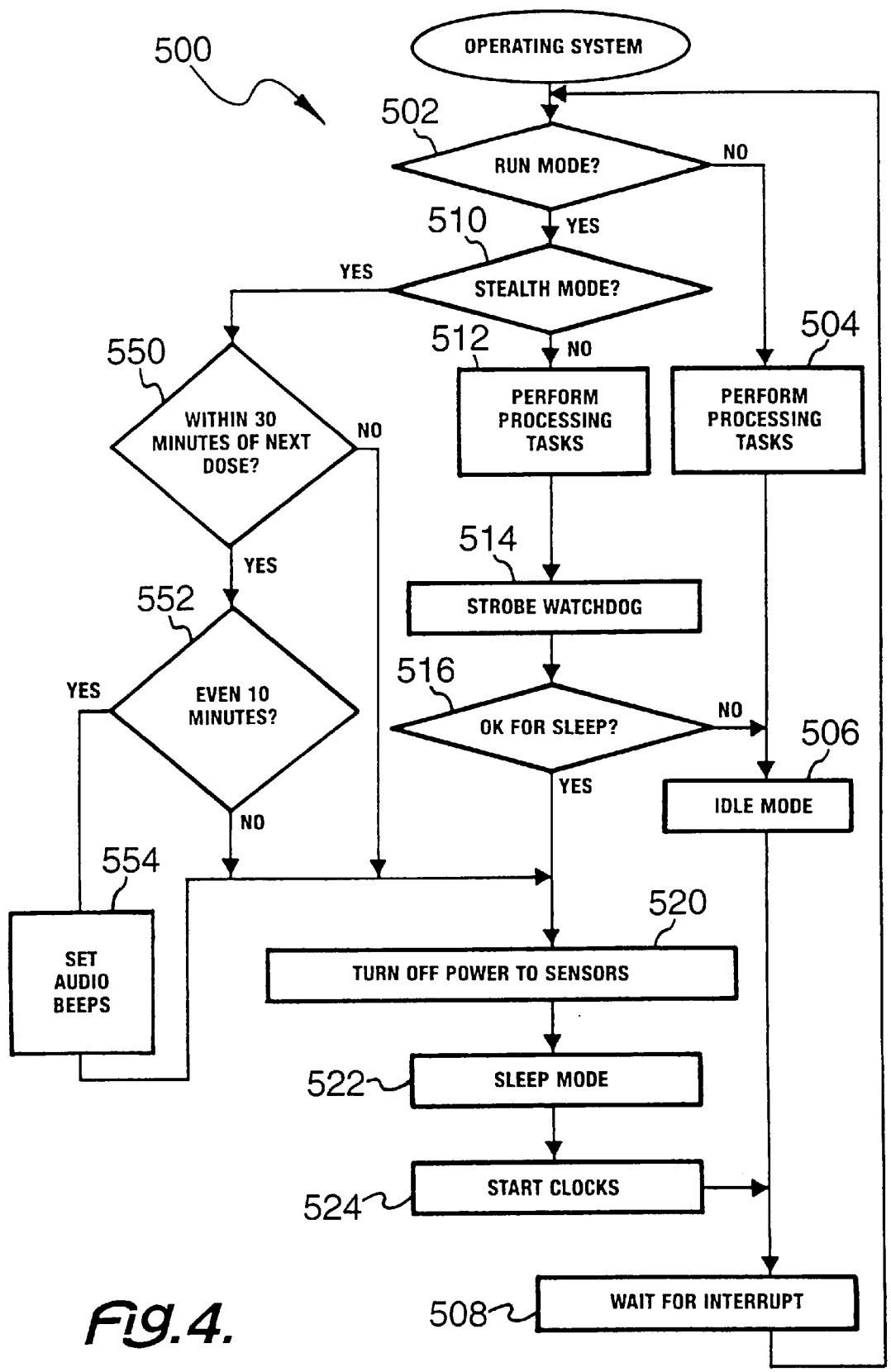
FIG. 4 is a flowchart of the operating system used by the infusion pump shown in FIG. 1.

A flowchart of the operating system 500 of the infusion pump 10 is illustrated in FIG. 4. The operating system 500 determines how the operations and tasks shown in the flowchart of FIG. 3 are performed. Referring to FIG. 4, if the pump is not operating in the run mode 460 as determined at step 502, the program branches to step 504 where any of the processing tasks of steps 402–436 (including called subroutines) of FIG. 3 may be performed. As described above, these tasks relate to the initial programming of the infusion pump 10 and are user-interactive. When there are no more of such tasks to be performed, for example, when the user has paused during the programming of the pump or has completed the pump programming, the program branches to step 506, where the controller 200 is placed in its idle mode, described above, via a software command. The controller 200 exits the idle mode upon the generation of an interrupt that is generated at step 508. The interrupt is periodically generated by the controller 200, for example, every 20 milliseconds.

Thus, when the pump is not in the run mode 460, the program cycles through steps 502–508 where it alternately performs at step 504 one or more of the processing tasks shown at steps 402–436 in FIG. 3 and is idled at step 506 to conserve battery power.

Under certain conditions, the pump may operate in the sleep mode described above. The pump may operate in the sleep mode when it is in the run mode 460 (FIG. 3) and is pumping below a relatively low infusion rate threshold, such as five milliliters/hour.

To deliver such a low infusion rate, the motor 51 is not activated continuously, but is instead turned on periodically (the motor 51 has a minimum rate at which it must be driven or else it will stall) to deliver a relatively small volume of liquid medicant, 50 microliters for example, and then is turned off. It is when the motor 51 is turned off when the controller 200 is placed in the sleep mode. When the programmed infusion rate is below the threshold, the frequency with which the motor turns on and off is determined by the programmed infusion rate. If the programmed infusion rate is above the threshold, the motor 51 will pump continuously.

Referring to FIG. 4, at step 510, if the pump is not in a stealth mode (described below), the program branches to a step 512 where a number of processing tasks relating to the infusion may be performed. At step 514, the watchdog timer 250 is strobed, and at step 516 the program determines whether the controller 200 may be placed in the sleep mode. As described above, the controller 200 may be placed in the sleep mode if the selected infusion rate is less than a predetermined threshold rate. There are also other conditions which must be satisfied. For example, the motor 51 cannot be active, an audio beep (in response to a key being pressed, for example) cannot be active, no timed functions can be active (such as a timed LED illumination), the backlight 220 cannot be on, and the display 16 cannot be scrolling text. If these conditions are satisfied, the program branches to a step 520 where the power to a number of sensors is turned off, and to step 522 where the controller 200 is placed in its sleep mode.

The controller 200 remains in the sleep mode until it is "awakened" by any of three occurrences: 1) any key being pressed, including the bolus-request key 332; 2) the watch-dog timer timing out; or 3) a one-second strobe generated by the real-time clock 210. In the absence of conditions 1) and 2), the controller 200 will be awakened every second by the strobe from the real-time clock 210. Upon being awakened, the internal clocks of the controller 200 are started at step 524, and the program branches to step 508 where it waits for the next interrupt generated by the controller 200.

The infusion pump 10 also has a stealth mode relating to the intermittent infusion mode of FIG. 3. In this mode, the pump 10 delivers an infusion spaced at relatively large time intervals, such as minutes or hours. Between infusions, the pump is placed in a stealth mode in which the controller 200 is put to sleep.

Figure 8:
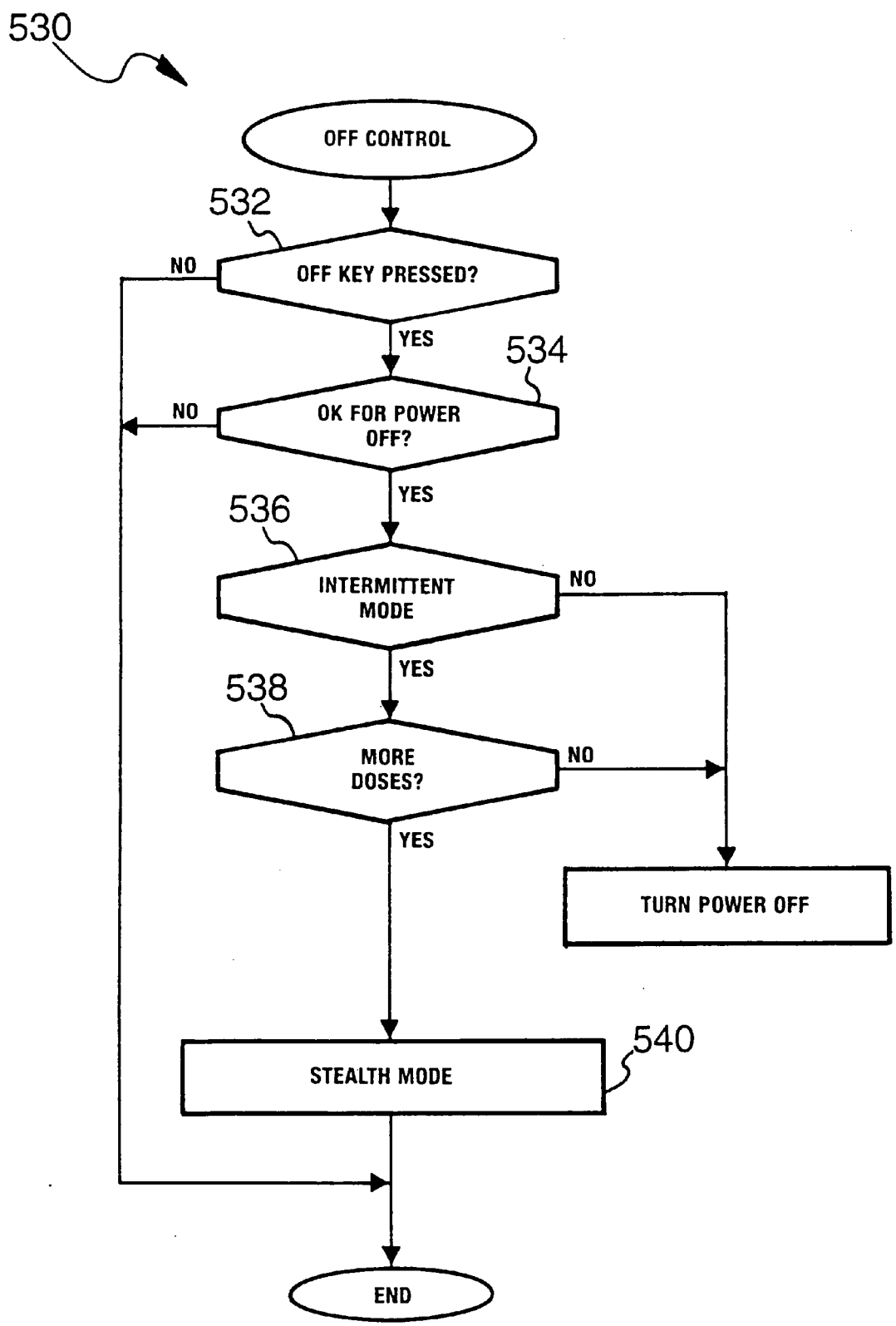
FIG. 8 is a flowchart of the operation of an on-off control routine of the infusion pump shown in FIG. 1.

FIG. 8 illustrates an off-control routine 530 that is periodically invoked to determine whether the on/off switch 288 (FIG. 2) of the infusion pump 10 has been turned off. In that case, as determined at step 532, the program branches to a step 534 where it determines if it is okay to turn the pump off (it is okay to turn the pump off as long as it is not in the run mode 460). If it is okay to turn the power off, the program branches to a step 536. If the pump 10 is not in the intermittent mode as determined at step 536, the power is turned off. If the pump is in the intermittent mode, the program branches to step 538, which determines whether there are any more periodic doses (infusions) to be made. If there are no more doses, the power is turned off.

If there is at least one additional dose, the pump 10 is placed in the stealth mode at step 540. Referring back to step 510 of FIG. 4, if the pump is in the stealth mode, the program branches to a step 550, which determines whether the next dose in the intermittent mode is scheduled within the next 30 minutes. If not, the program branches to steps 520–522 where the controller 200 is put to sleep.

If the next dose is within 30 minutes as determined at step 550, the program branches to step 552, where it determines whether the time until the next dose, or the time after that dose if not given, is a multiple of ten minutes. If it is, then the program branches to step 554, where the pump 10 generates an audible beep to the user as a reminder that the next dose is a multiple of ten minutes away. Thus, when the intermittent infusion mode is being used and the pump is in the stealth mode, the patient is given three audible warnings to reassure or warn the patient that the next dose is imminent, a first warning at 30 minutes prior to the dose, a second warning at 20 minutes prior to the dose, and a third warning at 10 minutes prior to the dose. If the next dose is not given on schedule, a fourth warning is generated at the time of the dose, and three additional warnings, spaced 10 minutes apart, are given after the time for the dose.

Data Storage and Recording

During programming and operation, the infusion pump 10 automatically records in the memory 204 all significant infusion data to generate a complete historical data record which can be later retrieved from the memory 204 and used for various purposes, including clinical purposes to aid in determining how effective a particular infusion therapy was and treatment purposes to confirm that the prescribed infusion was actually delivered.

The infusion data recorded in the memory 204 is set forth in Table 1 below. A number of events which trigger the storage of data are listed in the left-hand column of Table 1, and the infusion data that is recorded upon the occurrence of each event is listed in the right-hand column of Table 1. The time at which the infusion data is recorded, which is determined by the real-time clock 210, is also stored along with the infusion data.

TABLE 1

| EVENT | DATA RECORDED |
| --- | --- |
| Power On | Date and Time |
| Program | Infusion parameters. See Table 2. |
| Run | Infusion parameters. See Table 2. |
| Hold | Total Volume Infused |
| Restart | Time of Restart |
| Rate Changes | Total Volume Infused, Rate, Volume |
| Alarms | Total Volume Infused, Alarm Type |
| Infusion Complete | Total Volume Infused |
| Malfunctions | Total Volume Infused, Malfunction Type |
| Resume | Infusion parameters. See Table 2. |
| Maintenance Date | Date |
| Patient ID | Patient ID Number |
| Serial No. | Serial Number |
| Language Change | New Language |
| Lockout | Modes Locked Out |
| Pressure Select | New Pressure Setting |
| Bolus Request | Given/Not Given, Bolus Amount |
| Titration | New Parameters |
| Power Off | Time of Power Off |
| Version No. | Software Version Number |

Referring to Table 1, when the power to the infusion pump 10 is turned on, the date and time of the power turn-on is recorded. When the pump is completely programmed pursuant to one of steps 420, 424, 428, 432, or 436 (FIG. 3), the programmed infusion parameters are stored along with the time of such storage. The particular parameters that are stored depend upon which infusion mode was programmed. Examples of infusion parameters that are stored for the PCA infusion mode is illustrated in Table 2 below.

TABLE 2

| INFUSION MODE | INFUSION PARAMETERS |
| --- | --- |
| PCA | Infusion Mode |
|  | Basal Infusion Rate |
|  | Volume To Be Infused |
|  | Delay Time |
|  | Total Bag Volume |
|  | Bolus Dose Amount |
|  | Max. No. of Bolus Doses |
|  | Number of Doses |
|  | Dose Time |
|  | Dose Volume |
|  | KVO Rate |

When the pump enters the run mode at step 460 (FIG. 3), the time at which the run mode was begun, along with the parameters pursuant to which the infusion is performed, are stored. The pump also stores the time at which the hold key was pressed along with the total volume infused at the time the hold key was pressed. The pump stores any infusion rate changes, such as changes caused by switching from a continuous rate to a keep-vein-open (KVO) rate, or in the intermittent mode, changing from a KVO rate to a higher infusion rate, the new rate and the time at which the new rate started.

If any alarms are generated, the alarm type, the time at which the alarm occurred, and the total volume infused at the time of the alarm are recorded. If the infusion is completed, the program stores the time at which the infusion was completed along with the total volume infused. If there is a malfunction, the malfunction type, the time at which the malfunction occurred, and the total volume infused at the time of the malfunction are recorded.

If the infusion is resumed, when the pump is turned back on after having been turned off during an infusion, the time at which the infusion is resumed along with the infusion parameters are stored. Upon the completion of the programming of a lockout sequence, the time at which the programming of the lockout was completed is stored along with the infusion modes that were locked out. Upon the detection of a bolus request, the time at which the bolus was requested is stored, along with an indication whether the bolus was actually given and the amount of the bolus.

Patient Algorithm

Prior to assigning a particular infusion pump to a patient, the physician or caregiver programs in the patient's algorithm for automatically changing his PCA dose. The patient's algorithm defines the range of values for the basal dose, the bolus dose, the maximum amount of drug to be administered. The patient algorithm can increase or reduce the amount or duration of any of the PCA elements, depending on the patient's pain level, side effects and any impairment of the patient's functionalities.

The physician takes into account the patient's condition, the pain medication being provided and the range of medication to be provided based on the patient's pain level, side effects and impairment of functionality. The physician determines the course of therapy for the individual patient by changing the patient algorithm. For PCA, the patient algorithm includes a number of input parameters to control the basal rate and the bolus dose. The input parameters could include: a) pain level which could be captured by querying the patient directly or indirectly measuring the percentage of successful bolus request as discussed below; b) level of side effect including the frequency and intensity of vomiting and/or constipation; c) the restoration of physical function such as the limb movement and d) the effective time when the algorithm becomes active. The effective time is required to ensure that the system has adequate time to capture relevant information about the patient pain level, side effect and the restoration of bodily functions.

One embodiment of a patient algorithm for controlling basal rate and bolus dose is shown in Table 3 and Table 4 below.

TABLE 3

| Input | | | Output | |
|---|---|---|---|---|
| % of Successful Bolus Request | Side Effects | Restoration of Function | % Change to Basal Rate | % Change to Bolus Dose |
| 100 | No | No | −30 | 0 |
| 100 | No | Yes | −30 | −20 |
| 100 | Yes | No | −30 | 0 |
| 100 | Yes | Yes | −50 | −20 |
| 50 | No | No | +10 | +20 |
| 50 | No | Yes | +20 | +20 |
| 50 | Yes | No | 0 | +10 |
| 50 | Yes | Yes | 0 | +20 |

TABLE 4

| Input Pain Level | Output Side Effects | Restoration of Function | % Change to Basal Rate | % Change to Bolus Dose |
|---|---|---|---|---|
| 2 | No | No | −30 | 0 |
| 2 | No | Yes | −30 | −20 |
| 2 | Yes | No | −30 | 0 |
| 2 | Yes | Yes | −50 | −20 |
| 10 | No | No | +10 | +20 |
| 10 | No | Yes | +20 | +20 |
| 10 | Yes | No | 0 | +10 |
| 10 | Yes | Yes | 0 | +20 |

Other values for increasing or decreasing the basal rate may be used depending on the particular pain medication and other factors.

Capturing Pain Level Data

Table 3 requires input on Percent of Successful Bolus Request, Side Effects and Restoration of Function. As described below, Percent of Successful Bolus Request data is stored by the pump along with other pump information. This data can be accessed from memory. Percent of Successful Bolus Request information is used as an indirect measure of pain level. If the patient requests bolus requests after the maximum number has already been administered, this is an indication that the patient is in pain and needs either a higher basal rate, higher bolus dose or greater number of bolus doses, or a combination thereof.

Figure 6:
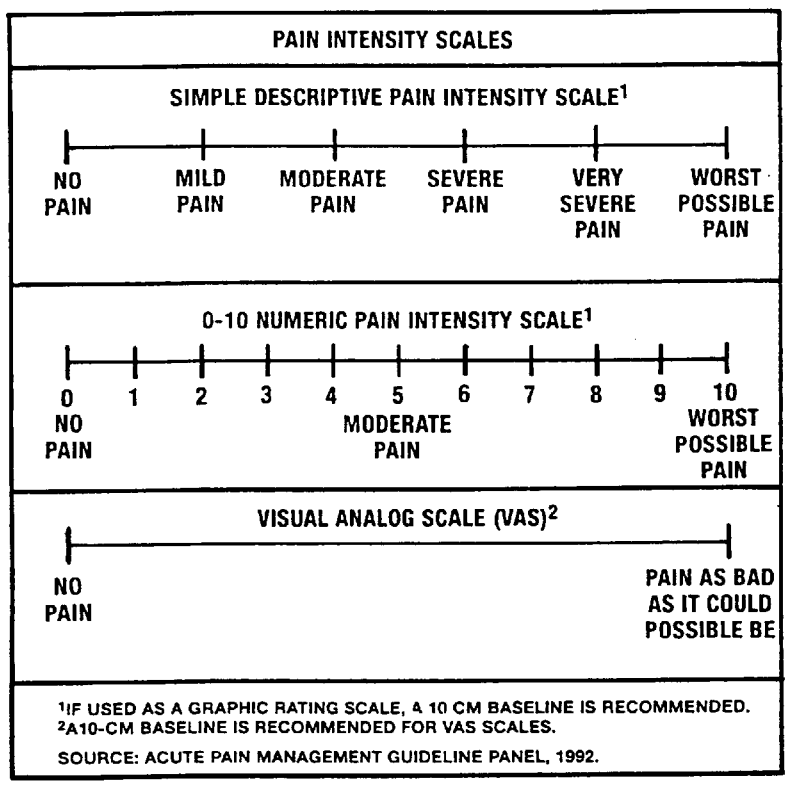
FIG. 6 shows sample pain intensity scales suggested by the Acute Pain Management Guideline Panel.

Alternatively, pain level information can be determined by querying the patient directly. For example, the patient can be queried at specific intervals, or whenever the patient requests a bolus dose, about pain level using a pain scale. Every hour the pump prompts the patient to enter a pain scale into the pump, based on a scale of from 0 to 10, with 10 being the highest level of pain. Instead of the 0 to 10 pain scale, an alternate pain scale suggested by the Acute Pain Management Guideline Panel is shown in FIG. 6. The information is stored in pump memory for use by the PCA mode modification routine. An attending caregiver may also ask the patient about pain level at regular or other intervals and enter the information into the patient's chart (for later input into the pump) or directly into the pump.

Capturing Data on Side Effects

Information for patient side effects is preferably acquired by prompting the patient to input responses to a series of specific questions. For example, for a patient receiving intravenous medication, the patient could be prompted to answer Yes or No to questions such as:

Cognitive Impairment

Nausea

For neuraxial medication, the patient could be prompted to answer Yes or No to questions such as:

Motor Impairment

Dizziness

This information can be requested each time the patient presses the bolus cord. Alternative methods of acquiring side effect data can be employed, such as, after a Yes response, asking the patient to expand on a scale of 0 to 10 for that side effect. The pump stores the results for use by the PCA mode modification routine.

Capturing Data on Function Impairment

As with data on side effects, data pertaining to the patient's function impairment can be obtained by prompting the patient to respond to a series of questions. Each time the patient requests a bolus dose, the pump with respond with a series of questions that the patient responds to with a Yes or No answer, and optionally, a rating of from 0 to 10. Examples of questions include:

Ability to move lower limbs

Restoration of bowel motility.

Automatically Modifying the PCA Program

Figure 5:
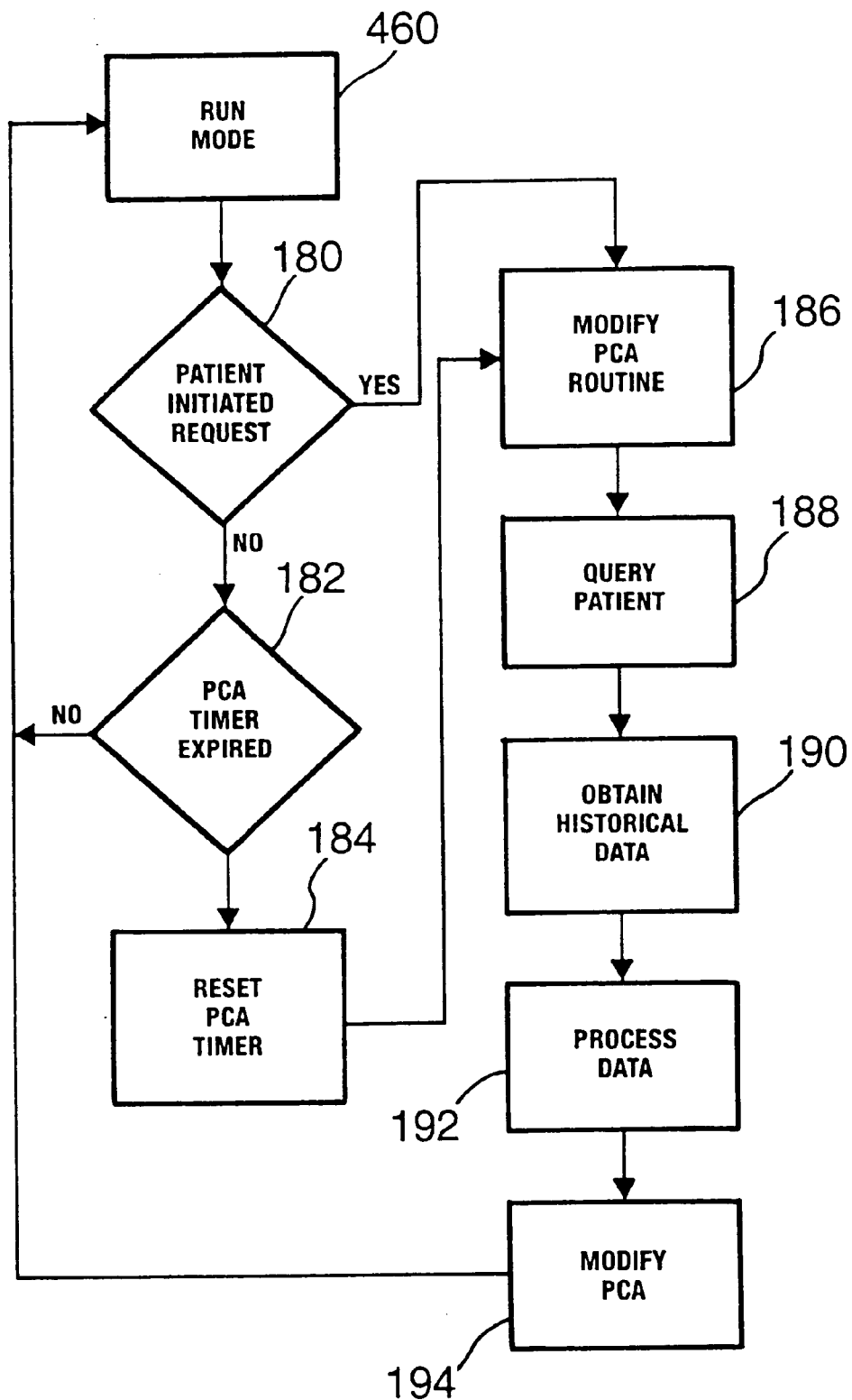
FIG. 5 is a flowchart of the operation to modify the PCA programming of the infusion pump shown in FIG. 1.

FIG. 5 shows the routine to modify the PCA programming of the infusion pump 10 Referring to FIG. 5, the PCA programmed values can be modified in one of two methods. In the first method, the PCA programmed values are modified by a patient initiated request while the pump is in the run mode at step 460. While in the run mode, the pump controller 200 periodically checks to see if the patient has initiated a request through bolus cord 15 and bolus button 17 (applied to bolus request switch 332) at step 180. If the answer is no, the pump controller 200 checks if a PCA time has expired. The pump may be programmed to check to see if the PCA programmed values should be modified on a periodic basis, say every hour, at step 182. If the answer is no, the routine loops back to step 460.

If the answer to step 180 or step 182 is yes, the routine branches to block 186, the PCA modification routine. In this preferred routine, the patient is queried at a step 188 on pain level, side effects and function impairment. Data is stored for use by the patient algorithm in evaluating whether or not the PCA programmed values should be changed. At step 190 the routine also checks stored historical values, such as number of successful bolus requests over time. At step 192 the routine processes the data according the patient algorithm and at step 194 modifies the PCA programmed values and returns to the Run Mode.

The invention allows the pump to automatically adjust basal rate and/or bolus rate to alleviate patient pain in the absence of the caregiver's intervention. The invention also adjusts the basal rate and quantity of boluses to reduce side effects and restore patient functionalities, improving the patient's overall quality of life. Calls to the caregiver by patients in pain can be reduced, reducing work load on caregivers.

Modifications and alternative embodiments of the invention will be apparent to those skilled in the art in view of the foregoing description. This description is to be construed as illustrative only, and is for the purpose of teaching those skilled in the art the best mode of carrying out the invention.

The details of the structure and method may be varied substantially without departing from the spirit of the invention, and the exclusive use of all modifications which come within the scope of the appended claims is reserved.

What is claimed is:

1. A method for automatically controlling the level of a patient's medication administered from a programmable infusion pump, comprising:

programming the infusion pump with a medication algorithm;

initiating an evaluation of the patient's medication;

obtaining information pertaining to the patient's condition;

obtaining information pertaining to the patient's current medication;

evaluating the patient's current medication and condition with the medication algorithm; and controlling administration of the patient's medication based on the evaluation.

2. The method of claim 1, wherein the step of obtaining information pertaining to the patient's current medication comprises storing information pertaining to the amount of medication administered to the patient over a predetermined period of time.

3. The method of claim 1, wherein the controlling administration of the patient's medication includes modification of a basal delivery rate, a bolus dose and a number of bolus allowed within a certain time frame.

4. The method of claim 1, wherein the step of obtaining information pertaining to the patient's condition further comprises storing the number of bolus requests made by the patient which exceed the maximum number of permitted boluses.

5. The method of claim 1, wherein the obtaining information pertaining to the patient's condition further comprise the steps of querying the patient regarding the patient's pain level, side effects and impairment of functionalities.

6. The method of claim 1, wherein the step of obtaining information pertaining to the patient's condition further comprises the step of providing an evaluation of the patient's side effects.

7. The method of claim 1, wherein the step of obtaining information pertaining to the patient's condition further comprises the step of providing an evaluation of the patient's impairment of functionalities.

8. A routine for operating an infusion pump to automatically control the level of a patient's medication, the infusion pump comprising a controller for executing the routine and a memory for storing the routine, responsive to a request for an evaluation of the patient's current medication; comprising:

a set of patient-specific, predetermined ranges of medication stored in the memory;

a procedure for obtaining information pertaining to the patient's pain level and storing the patient's pain level information automatically;

a procedure for obtaining information pertaining to the patient's side effects and storing the patient's side effect information automatically;

a procedure for obtaining information pertaining to the patient's impairment of functionalities and storing the patient's impairment of functionalities information automatically;

a procedure for obtaining information pertaining to the patient's current medication;

a procedure for evaluating stored information of the patient's current medication, pain level, side effects and impaired functionalities with the stored set of patient-specific, predetermined ranges of medication; and a procedure for automatically modifying delivery of the patient's medication based on the evaluation.

9. An infusion pump for administering a liquid medicant to a patients comprising:

a liquid injection device adapted to be connected to the patient;

a conduit connected to the liquid injection device;

a pumping mechanism for pumping the liquid medicant through the conduit and into the patient via the liquid injection device;

a controller for controlling the pumping mechanism, wherein the controller controls the amount of liquid medicant administered to the patient;

a memory storing a set of patient-specific, predetermined rates and amounts of liquid medicant to be administered to the patient;

a data acquiring routine for obtaining information pertaining to the patient's pain level, side effects and impairment of functionalities; and a control routine for processing the data pertaining to the patient's pain level, the patient's side effects, the patient's impairment of functionalities, and a current rate and amount of liquid medicant being administered to the patient and for automatically changing the rate and amount of the liquid medicant to be administered to the patient in accordance with the set of patient-specific, predetermined ranges of medication.

10. The infusion pump of claim 9 further wherein the memory stores data regarding the liquid medicant administered to the patient over a predetermined period of time and wherein the modification routine processes the data regarding liquid medicant administered to the patient.

11. The infusion pump of claim 10 wherein the current rate and amount of liquid medicant being administered to the patient comprises a basal delivery rate, a bolus dose and a number of bolus allowed within a certain time frame.

12. The infusion pump of claim 11 wherein data pertaining to the patient's pain level comprises the number of bolus requests made by the patient which exceed the maximum number of boluses.

13. The infusion pump of claim 11 wherein data pertaining to the patient's pain level, side effects and impairment of functionalities comprises data stored in response to querying the patient regarding the patient's pain level, side effects and impairment of functionalities.

14. The infusion pump of claim 11 wherein data pertaining to the patient's side effects comprises data stored from an independent evaluation of the patient's side effects.

15. The infusion pump of claim 11 wherein data pertaining to the patient's impairment of functionalities comprises data stored from an independent evaluation of the patient's impairment of functionalities.

16. A method for automatically controlling the level of a patient's medication administered from a programmable infusion pump, comprising:

programming the infusion pump with a set of patient specific, predetermined ranges of medication;

evaluating the patient's current medication and recording the patient's current medication in the infusion pump;

evaluating the patient's physiological conditions and recording the patient's physiological conditions in the infusion pump; and controlling administration of the patient's medication based on the evaluation of the patient's current medication and physiological conditions as compared with the programmed predetermined ranges of medication.

17. The method of claim 16, wherein the evaluating the patient's physiological conditions step includes evaluating the patient's pain level, the patient's side effects and the patient's impairment of functionalities.

18. The method of claim 16, further comprising querying the patient about his physiological conditions; and storing the patient's responses.

* * * * *